United States Patent
Eyal et al.

(10) Patent No.: US 6,667,417 B2
(45) Date of Patent: *Dec. 23, 2003

(54) PROCESS FOR THE RECOVERY OF LACTIC ACID

(75) Inventors: Aharon Meir Eyal, Jerusalem (IL); David Witzke, Eden Prairie, MN (US); Rod Fisher, Eden Prairie, MN (US)

(73) Assignee: Yissum Research Development Company of the Hebrew University of Jerusalem, Jerusalem (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/367,618

(22) PCT Filed: Feb. 12, 1998

(86) PCT No.: PCT/US98/02695

§ 371 (c)(1),
(2), (4) Date: Nov. 19, 1999

(87) PCT Pub. No.: WO98/37050

PCT Pub. Date: Aug. 27, 1998

(65) Prior Publication Data

US 2002/0128508 A1 Sep. 12, 2002

(30) Foreign Application Priority Data

Feb. 21, 1997 (IL) .................................................. 120279

(51) Int. Cl.[7] .......................... C07C 51/42; C07C 59/08
(52) U.S. Cl. .................. 562/485; 580/589; 580/593
(58) Field of Search ................................ 562/589, 580, 562/485, 593

(56) References Cited

U.S. PATENT DOCUMENTS

| 2,143,361 | A | | 1/1939 | Morgan et al. ............. 260/535 |
|---|---|---|---|---|
| 4,275,234 | A | | 6/1981 | Baniel et al. ................ 562/584 |
| 4,323,702 | A | * | 4/1982 | Kawabata et al. ........... 562/485 |
| 4,444,881 | A | * | 4/1984 | Urbas ........................ 435/139 |
| 4,720,579 | A | * | 1/1988 | Kulprathipanja ............ 562/580 |
| 4,924,027 | A | * | 5/1990 | Kulprathipanja et al. ... 562/580 |
| 5,132,456 | A | * | 7/1992 | King et al. ................. 562/593 |
| 5,210,296 | A | * | 5/1993 | Cockrem et al. ........... 562/589 |
| 5,510,526 | A | * | 4/1996 | Baniel et al. ............... 562/580 |

FOREIGN PATENT DOCUMENTS

| DE | 678428 | | 7/1939 |
|---|---|---|---|
| EP | 0393818 | * | 10/1990 |
| GB | 907321 | | 7/1958 |

* cited by examiner

*Primary Examiner*—Alan L. Rotman
*Assistant Examiner*—Taylor V. Oh
(74) *Attorney, Agent, or Firm*—Ladas & Parry

(57) ABSTRACT

The invention provides a process for producing lactic acid from a medium containing an alkaline earth-metal salt of lactic acid, comprising (a) reacting a conjugated base of an alkali metal from a subsequent step with the medium to form a water soluble alkali metal lactate salt and a basic compound of the alkaline earth metal; (b) separating the water soluble alkali metal lactate salt and the basic compound of the alkaline earth-metal; (c) splitting the water soluble alkali metal lactate to form a conjugated alkali metal base and a lactic acid product, which product is selected from the group consisting of lactic acid; and (d) separating the conjugated alkali metal base and the lactic acid product; (e) reusing the separated conjugated alkali metal base or the product in the step (a); and (f) reusing the basic compound of the alkaline earth metal, separated in step (b) to form an alkaline earth metal salt of lactic acid.

47 Claims, No Drawings

PROCESS FOR THE RECOVERY OF LACTIC ACID

The present invention relates to a process for producing lactic acid. More particularly the present invention relates to a process for producing lactic acid and products thereof, from a medium containing an alkaline earth-metal salt of lactic acid, especially when the medium results from a fermentation of at least one carbohydrate.

Lactic acid has long been used as a food additive and in various chemical and pharmaceutical applications. More recently, lactic acid has been used in the making of biodegradable polylactic acid polymers as a replacement for present plastic materials, as well as for various new uses in which biodegradability is needed or desired. Accordingly, there is an ever-increasing demand for lactic acid. The present invention aims at meeting this demand by providing an efficient and environmentally friendly process for producing lactic acid, which avoids the consumption of bases and acids and substantially reduces, if not eliminates, the formation of waste, and/or of by-product salts.

The production of lactic acid is commonly carried out by fermentation of a strain of the bacterial genus Lactobacillus, and more particularly, for example, by the species *Lactobacillus delbrueckii*, or *Lactobacillus acidophilus*. In general, the production of lactic acid by fermentation in a fermentation broth is well known in the art. The fermentation substrate consists of carbohydrates together with suitable mineral and proteinaceous nutrients. Because the lactic acid-producing micro-organisms are inhibited in a strongly acidic environment, the pH of the fermentation broth is usually kept above 4.5, preferably within the range of about 5.0 to 7.0, more preferably within the range of about 5.5 to 6.5, and most preferably within the range of about 6.0 to 6.5., although fermentation in a pH range of about 3.8–4.5 has also been carried out. To maintain this pH level, suitable water-soluble basic substances, or agents, that are non-toxic to the acid-producing microorganism, are commonly added as a neutralizing agent to the fermentation broth in order to neutralize the lactic acid being produced. Preferred bases are those of alkaline earth metals, more preferably those of calcium or magnesium, most preferably calcium bases selected from the group consisting of carbonates, bicarbonates and hydroxides.

In such processes lactate salts are formed rather than lactic acid, even though lactic acid, as such, or derivatives thereof, e.g. lactic acid condensation products are usually the desired product. (In the following, if not specified otherwise, the term lactic acid will refer to both the acid and its non-salt derivatives such derivatives include lactide, lactoyl lactate, low molecular weight oligomers of lactic acid, polylactic acid and lactic acid esters.) Therefore, many processes were developed for the recovery of lactic acid from its salts, particularly calcium lactate, that forms in fermentations using calcium bases as neutralizing agents. In a common industrial practice sulfuric acid is added to fermentation liquors containing Calcium Lactate ($CaLa_2$) to form gypsum and to liberate the lactic acid. The latter is purified from impurities present in the broth and concentrated. The main disadvantage of this process is that it irreversibly consumes the calcium base and sulfuric acid and requires the disposal of large volumes of gypsum. Such disposal of large volumes of gypsum is unacceptable, particularly for the production of an environmental-friendly product, such as, the biodegradable polylactic acid.

DE-C-678 428 describes producing water-free lactic acid and anhydride by treating a solution of ammonium or sodium lactate, wherein said solution is obtained by reacting calcium lactate with ammonium or sodium carbonate.

Nakanishi and Tsuda, in JP 46/30176, proposed production of 1-butyl lactate by extraction of an acidified crude fermentation broth with 1-butanol, followed by esterification of the extract phase. BASF (EP 159 285) proposes a similar process with isobutanol, to form isobutyl lactate. The process of WO 93/00440, assigned to DuPont, comprises the steps of: (1) simultaneously mixing a strong acid, an alcohol, and a concentrated fermentation broth, which contains mainly basic salts of lactic acid, which react to form a crystal precipitate comprising basic salts of the strong acid and an impure lactate ester of the alcohol; (2) removing water from the mixture as a water/alcohol azeotrope which can be accomplished either sequentially or substantially simultaneously with step (1); (3) removing the crystal precipitate from the mixture; and (4) distilling the impure lactate ester to remove impurities and recovering the high purity ester.

In these processes, as in the case of gypsum, a strong mineral acid is used as an acidulant and an undesired by-product salt is formed. Many efforts have recently been made to recover lactic acid from its salts formed through fermentation without formation of by-products. In order to achieve this result, the lactate salt is converted to lactic acid, or a derivative thereof, and to a conjugated base or a basic compound of the lactate salt cation. (In the following, if not specified otherwise, such conjugated base or a basic compound of the lactate salt cation or a mixture thereof, formed in such conversion, is referred to as the conjugated base.) Such conversion is referred to in the following as salt splitting. The salt splitting conjugated base is recycled as is or after further conversion and used as a neutralizing agent in the fermentation.

Examples of such salt splitting processes for lactic acid are given in the many patents dealing with water splitting electrodialysis and in others, such as: U.S. Pat. No. 5,132,456 (King); U.S. Pat. Nos. 4,444,881 and 4,405,717 (Urbas); U.S. Pat. No. 5,252,473 (Walkup); Israeli patent Application 117,232 (Eyal) and U.S. Pat. No. 5,510,526 (Baniel).

Splitting of a salt to its acid and conjugated base requires introduction of energy to compensate for the neutralizing energy. If formation of no by-products is aimed at use of chemical energy of strong acid-base neutralization, should be avoided and other energy sources are needed to drive the reaction forward. Electrical energy is the driving force in those processes using water splitting electrodialysis. Bipolar membranes are used. Such membranes are very sensitive to impurities and applying them to fermentation products requires costly purification operations. Thus, in most alternatives, thermal energy is the main driving force for the salt splitting. In the case of salts of a relatively strong carboxylic acid, such as lactic acid (pKa=3.86), the energy needed is high. That is particularly true in those cases in which a free acid is formed in the salt splitting. Thus, splitting of sodium lactate to lactic acid and sodium hydroxide by the use of thermal energy seems impractical. Such splitting is somewhat easier in the case of ammonium lactate in which case the regenerated, conjugated base, ammonia, is a relatively weak one. Another advantage of the use of ammonia is its volatility which makes it easier to remove from the reaction mixture. Yet, the process for salt splitting of ammonium lactate involves very high temperatures (about 170° C.) and pressures (about 100 atm.) as in the Walkup patent, ibid. and/or a relatively low yield in a very complicated process with some uncontrolled reactions as in the King patent, ibid.

A way to reduce the load on the thermal energy for lactate salt splitting is to combine it with the formation of a water immiscible product, i.e. formation of a water immiscible conjugated base. This approach has two main advantages:
(a) it removes the base formed from the reaction mixture and thereby assists in shifting the reaction forward; and,
(b) it uses the crystallization energy of the conjugated base as a driving force, thereby reducing the thermal energy consumption.

It is very difficult to combine into one step thermal energy driven splitting of a lactate salt to lactic acid and a conjugated water immiscible base. The prior art does it indirectly in multiple-step processes. Thus, in Urbas' patents, ibid. a water soluble tri-alkyl amine carbonate is added to the calcium carboxylate containing solution. Calcium carbonate crystallizes out of the solution and the tri-alkyl amine carboxylate is formed. The latter is then decomposed thermally. This process has two major drawbacks related to the use of tri-alkyl amine:
(a) Tri-alkyl amine is a volatile, water soluble amine, which is difficult to handle and an undesirable chemical, particularly when a food grade product is sought; and,
(b) this amine is a relatively strong base, stronger than ammonia and thermal decomposition of its lactate is complicated and problematic as described in U.S. Pat. No. 5,132,2456.

Is there a possibility to solve these problems by using, instead of Urbas' water soluble strong tri-alkyl amine, a water immiscible and much weaker amine? As shown by Miller et al. (Ind. Eng. Chem. Res. 1996, 35(4) 1156–42), the yield of a process using a water immiscible, relatively weak amine is low. A solution to the problem was found in Baniel's U.S. Pat. No. 5,510,526, splitting sodium lactate rather than calcium lactate and forming sodium bicarbonate as the conjugated base rather than calcium carbonate. Sodium lactate is much more soluble and allows for feeding to the process a very concentrated lactate salt solution. Thus, Baniel found a way to efficiently combine tri-alkyl amine several driving forces in his process; thermal energy, the (chemical) crystallization energy of $NaHCO_3$, the (chemical energy) of high reagent concentration, the (mechanical) energy of $CO_2$ pressurization and the thermal sensitivity of carboxylic acid extraction (U.S. Pat. No. 4,275,234).

In order to make use of high concentration as a driving force in processes such as that of Baniel, a water soluble lactate salt is preferred over the much less soluble calcium lactate, which is the industrial product. Using an alkali metal base as a neutralization agent in fermentation was tested and found to be problematic. Therefore the preferred option is to use an alkaline earth-metal base, preferably a calcium base, as a neutralizing agent and convert the lactate salt formed to a water soluble alkali metal lactate. (In the following, if not specified otherwise, the term base would include both base and basic compounds and the term conversion will refer to the reaction of converting an alkaline earth-metal base to a water soluble alkali metal lactate.) Such conversion should result in the regeneration of the alkaline earth metal base for recycle to the fermentation. Furthermore, overall, the conversion should not consume a reagent and/or form a by-product. The reagent used for effecting this conversion should be obtained from a previous step in the process, which means that it should be formed in such a previous step. In order to avoid an over complicated process, that reagent should be the conjugated base or should be easily formed from such a conjugated base.

Thus, in order for the fermentation to use the preferred neutralizing base and for the overall process to avoid the consumption of reagents and the formation of undesired by-products, an alkaline earth-metal base should be used as a neutralizing base in the fermentation, the alkaline earth-metal lactate formed should be reacted with an alkali metal based conversion reagent (a reagent needed to effect the desired conversion) to convert it to an alkali metal lactate and to a base of an alkaline earth metal, this base of an alkaline earth metal, as is, or after modification, should be suitable for recycle as a neutralizing base in the fermentation, the alkali metal lactate salt should be split in a process that forms lactic acid at the desired purity and a conjugated base, which conjugated base, as is, or after modification, should be suitable to serve as a conversion reagent.

This becomes even more complicated considering the above described preference to a salt splitting process that forms a water immiscible conjugated base. Sterzel (U.S. Pat. No. 5,453,365) describes a process in which an alkaline earth-metal carbonate is used as a neutralizing agent in lactic acid fermentation, the resulting fermentation liquor is adjusted to pH 7 to 13 by the addition of $NH_3$ and $CO_2$, the resultant precipitates are separated, and the resulting purified ammonium lactate solution is esterified with an alcohol. In such process ammonia is reformed and can be used as a reagent in the conversion of the alkaline earth-metal lactate to ammonium lactate. The reformed ammonia is recovered from the vapor phase, practically free from fermentation resulting impurities. This is, however, not the case when a water immiscible conjugated base is formed in the salt splitting process. Many of the impurities in the fermentation liquor may co-precipitate and thereby be recycled to the conversion process. In such a step they could transfer to the alkaline earth-metal base formed and be recycled with it to the fermentation. As a result, impurities are expected to build up in the system to a level that interfere with both the fermentation and the recovery of pure lactic acid or products thereof.

This problem is even more pronounced in cases in which liquid—liquid extraction is used in the salt splitting step, as in Baniel's process. The water immiscible, long-chain amine containing extractant could coat the crystals of the precipitating conjugated base or included therein by inclusion and be recycled thereby to the fermentation. Several studies have shown a major toxic effect related to such long-chain amine presence in the fermentation (Yu Ming et. al. Int. Solv. Ext. Conf. 517–18, 1983).

Kimmel and Dudta described (Rev. Chim., Bucharest, 11,47–8, 1960) the conversion of fermentation formed calcium lactate to sodium lactate for use as a replacer for glycerides in applications such as water anti-freeze, The conversion is conducted in a reaction with sodium carbonate to form calcium carbonate as a by-product. The conversion yield shortly after the precipitation was found to be strongly dependent on temperatures: 97.27%, 97.65%, 98.16%, 98.80% and 99.45% at temperatures of 20° C., 40° C., 60° C., 80° C. and 100° C. respectively. After five days the yield at 20° C. reached that at 100° C. The authors teach that the concentrations of the reacting compounds are very important for several reasons. At too high concentrations a strong foam formation interferes with the reaction. In addition, significant amounts of the desired product, sodium lactate are found in the precipitated calcium carbonate. According to the authors both reagents should be introduced in a solution, the optimal concentrations of which are 20% for the calcium lactate and 25% for the sodium carbonate. At these conditions, 11% of the lactate are found in the precipitate. These lactate levels could be recovered by washing with water and addition of the wash water to the product solution. The authors studied the reaction on calcium lactate crystals obtained from fermentation (I) and on fermentation liquor (II). They found that purification by the addition of $FeSO_4$ is needed. On such addition iron lactate is formed in the solution and gypsum precipitates. Then lime is added to convert the iron lactate to calcium lactate and to precipitate $Fe(OH)_2$. In case (I) the amount of $FeSO_4$ to be added is 10% of the equivalent amount of the calcium lactate. In case (II) two stages were needed, each using 10% equivalents of $FeSO_4$.

This article points out major difficulties. The foam formation would be even higher in the preferred embodiment of the present invention, where the sodium base is sodium bicarbonate rather than carbonate—the amount of $CO_2$ formed will double. In addition, according to another preferred embodiment of the present invention this sodium base is of a relatively low solubility and is separated by crystallization. Using it in a solid form from would cause sodium lactate product losses into the calcium carbonate as explained by the article. Furthermore there could be difficulties due to precipitation of calcium carbonate on sodium bicarbonate crystals. Dissolving the sodium base to form a 25% solution and washing of lactate values from the calcium carbonate, as recommended in the article would dilute significantly the solution of the alkali metal lactate, which would increase the energy cost related to the salt splitting step.

Another major difficulty is related to the purification step. According to a preferred embodiment of the present invention, the lactic acid formed needs to reach high purity, for example polymer grade. A purification step as suggested could make the overall uneconomic and problematic for two main reasons (a) reagents are consumed ($FeSO_4$ and lime) and by products are formed ($Fe(OH)_2$ and gypsum) and (b) some iron would probably remain in the sodium lactate solution (by dissolution, possibly enhanced by the complexing capacity of the lactate) and could contaminate the final product. It could also interfere in lactic acid condensation to polylactic acid.

Another potential problem is related to another preferred embodiment described above. One of the main purposes for converting the alkaline earth-metal lactate to alkali metal lactate is the enhancement of the salt splitting by preconcentration. Some of the alkaline earth metal is expected to be left in the solution after conversion and on concentration of said solution would form scale that could block the evaporator. Complete removal of the alkaline earth-metal ions is expected to be hindered by the strong complexing capacity of the lactate ion.

Surprisingly, It was found that an economic and relatively simple process can be effected based on fermentation to an alkaline earth-metal lactate, conversion of the latter to a water soluble alkali metal lactate and splitting the latter with internal recycle of the conjugated base to the conversion step which results in the formation of an alkaline earth-metal base recycled as a neutralizing agent to the fermentation.

Thus according to the present invention and with the above state of art in mind, there is now provided a process for producing lactic acid and products thereof from a medium containing an alkaline earth-metal salt of lactic acid, comprising:
(a) reacting a conjugated base of an alkali metal from a subsequent step with said medium to form a water soluble alkali metal lactate salt and a basic compound of said alkaline earth metal;
(b) separating said water soluble alkali metal lactate salt and said basic compound of said alkaline earth metal;
(c) splitting said water soluble alkali metal lactate to form a conjugated alkali metal base and a lactic acid product, which product is selected from the group consisting of lactic acid, a derivative thereof and combinations thereof;
(d) separating said conjugated alkali metal base and said lactic acid product;
(e) re-using said separated conjugated alkali metal base or a product thereof in step (a); and,
(f) re-using said basic compound of said alkaline earth metal, separated in step (b), or a product thereof to form an alkaline earth-metal salt of lactic acid.

In an especially preferred embodiments of the present invention said medium results from a fermentation of at least one carbohydrate, and said alkaline earth-metal base separated in step (b), or a product thereof is used as a neutralizing agent in said fermentation.

As stated, according to the present invention, lactic acid and products thereof, are produced from a medium containing at least one alkaline earth-metal salts of lactic acid. Alkaline earth-metal salts of lactic acid are formed in reaction between alkaline earth metal containing compounds and lactic acid or its compounds. Preferably said alkaline earth metal containing compounds are alkaline earth metal bases. More preferably these bases are selected from the group consisting of hydroxides, oxides, carbonates, bicarbonates or mixtures thereof. Preferably, said alkaline earth metal is selected from the group consisting of calcium and magnesium and most preferably it is calcium.

Furthermore, as stated, in a preferred embodiment of the present invention said at least one alkaline earth-metal salts of lactic acid is a fermentation product and said medium containing it is a fermentation liquor, or is obtained from such a fermentation liquor. The pH of said lactic acid fermentation is adjusted by adding a base or a basic compound to the fermentation medium to effect direct neutralization of lactic acid values. Alternatively, the fermentation medium is contacted with a water immiscible base, such as a basic resin or a high molecular weight amine, and lactic acid formed in the fermentation is bound to said water immiscible base. The latter is then reacted with another base or basic compound to effect indirect neutralization whereby there is formed the corresponding lactate salt and the water immiscible base is reformed. According to a preferred embodiment of the present invention a basic compound of alkaline earth metal, preferably calcium or magnesium and most preferably calcium, which basic compounds is preferably an oxide, hydroxide, carbonate, bicarbonate or a mixture thereof, most preferably carbonate is used as a neutralizing agent in said fermentation, either directly or indirectly. Thus, at least part of the fermentatively formed lactic acid in the staring medium is in the form of a salt of said alkaline earth metal.

Said alkaline earth-metal lactate could be fully dissolved in the medium containing it. Alternatively, part of it is in a solid form. In a preferred embodiment, this medium is treated prior to said reaction in step (a). In the preferred embodiment in which this medium is the fermentation liquor, such pretreatment includes biomass removal by methods such as, decantation, centrifugation, flocculation, filtration, or ultra-filtration. Another pre-treatment could be purification of the alkaline earth lactate preferably by a step selected from the group consisting of washing, recrystallization from an aqueous solution, recrystallization from a solvent solution, treating its solution with active carbon, absorbent or ion exchanger and a combination thereof. Still another pre-treatment is the separation of free lactic acid, if present in said medium.

Said medium containing said alkaline earth-metal lactate is reacted with a conjugated base of an alkali metal from a subsequent step. Said alkali metal is preferably sodium or potassium and most preferably sodium. Said base is preferably selected from the group consisting of hydroxides, oxides, carbonates, bicarbonates and mixtures thereof, and the use of a bicarbonate is especially preferred. In this reaction at least one basic compound of the alkaline earth metal and the alkali metal lactate are formed. Typically, the solubility of said alkali metal lactates is higher than that of said alkaline earth-metal lactates and the solubility of said alkali metal base is higher than that of said alkaline earth-metal base. Thus, the reaction is preferably driven forward by crystallization energy.

The alkaline earth-metal base is separated from the alkali metal lactate by methods known per se, preferably by crystallization.

As will be realized, step (a) can be conducted in a continuous mode or in a semi-continuous mode and preferably a crystal habit modifier is used in step (a).

Alkaline earth-metal ions remaining immersed in the reaction medium may interfere in the following steps, particularly in the splitting step (c) and especially when preceded by a step of concentrating the alkali metal lactate solution. Surprisingly, it was found that a conversion yield of at least 99.9% is achieved and that in spite of the very strong complexation capacity of the lactate, the alkaline earth-metal ion concentrations in the reaction medium could be lowered to less than 100 ppm Preferably, the temperature in said reaction is between 60° C. and 90° C. the pH of said reaction is maintained between 5 and 10 most preferably between 7 and 9, and the pH at the end of the reaction is preferably between 7 and 9. Preferably, the equivalent ratio between said alkaline earth-metal lactate in said medium and said alkali metal base (the ratio between the number of equivalents of each) is between 1:2 and 2:1. If desired, the reaction in step (a) can be completed by addition of another alkali base, preferably a base of the same alkali metal. The preferred final pH is determined by the need to lower the alkaline earth metal content to a level that will not interfere in the following steps, in addition to other considerations. Those could include de-naturation of peptidic and proteinic contaminants for improved removal in subsequent steps and precipitation of impurities such as silicates and metals (in oxide form). Based on these considerations, a person versed in the art could determine the preferred final pH.

Preferably, said conjugated base of an alkali metal is added in a solid form and the water content of the reaction in said step (a) is adjusted so that the concentration of the alkali metal lactate formed is between 10 and 50% by weight.

Preferably, said reaction in said step (a) is conducted in the presence of a carbonate source selected from the group consisting of $CO_2$, bicarbonate anion, carbonate anion and a combination thereof. In those preferred cases where the alkali metal base is a carbonate or a bicarbonate, particularly in the latter case, said reaction in said step (a) is preferably conducted at a sub-atmospheric pressure.

The alkaline earth base formed is preferably selected from the group consisting of hydroxides, oxides, carbonates, bicarbonates, and mixtures thereof, most preferably in carbonate. It is separated from the reaction medium, preferably by crystallization and re-used. In the case of lactic acid fermentation it is preferably used as a neutralizing agent in the fermentation. If required, it is purified prior to re-use, e.g. by washing. It can be re-used as such or after modification. Thus, in the event that this base is a carbonate, it can be converted by calcination to its oxide form and then, if required, to its hydroxide form.

In a most preferred embodiment, said medium, containing said alkaline earth metal lactate, is a fermentation liquor obtained in a fermentation process using calcium carbonate as a neutralizing agent, and most of the lactate present in said fermentation liquor is calcium lactate. Most preferably, said base of an alkali metal is sodium bicarbonate or carbonate and the products of said reaction in step (a) are sodium lactate, which remains in the aqueous solution, $CO_2$, which evolves out of the reaction medium, and calcium carbonate, which precipitates out of said medium. Said calcium carbonate is separated, purified if needed, e.g. by washing, and re-used as a neutralizing agent in fermentation.

The alkali metal lactate formed in the reaction of step (a) and separated in step (b) is obtained in a relatively pure form and can be introduced into the splitting process of said step (c), as is, or after some simple purification steps, such as contacting with an active carbon, or some other adsorbent, contact with an ion exchanger and combinations thereof. If desired, its composition can be adjusted by operations such as additional filtration and pH adjustment. Concentrating the solution of the alkali metal lactate prior to step (c) is helpful. It was found that at the preferred conditions for step (a), the amount of alkaline earth-metal ions remaining in the solution after said steps (a) and (b) is small and that it does not interfere with concentration of the solution to at least 50% or even 70% w/w.

In the splitting of step (c) the alkali metal lactate is converted to a lactic acid product and to a conjugated base, which lactic acid product is selected from the group consisting of lactic acid, a derivative thereof, and a combination thereof. Said derivative include condensation products such as lactide, lactoyl lactate, poly lactate acid and lactic acid esters and other non-salt derivatives. The conjugated base is preferably selected from the group consisting of hydroxides, bicarbonates, carbonates and mixtures thereof, most preferably bicarbonate. Any salt splitting process suitable for alkali metal lactate can be used, e.g. electrodialytic salt splitting to lactic acid and the alkali metal hydroxide. Preferred, however, are those salt-splitting processes forming conjugated bases of relatively low solubility in water, preferably solubility of less than 20% w/w at the temperature of said salt splitting. In a most preferred embodiment, the conjugated base precipitates out during said salt splitting in said step (c). Most preferable are those processes that form sodium bicarbonate as the conjugated base.

The separation between the lactic acid product and the conjugated base is effected by methods known per se, most preferably by crystallization of the base. Said separated conjugated base is recycled to the reaction in step (a) as is, or after modification. An example for such modification is the thermal decomposition of sodium bicarbonate in the presence of water to sodium carbonate and $CO_2$. If desired said conjugated base, as is, or after modification, is purified prior to recycling to the reaction in step (a).

In a preferred embodiment, the lactic acid product formed in step (c) is bound to a water immiscible base, preferably selected from the group consisting of basic resins and extractants consisting of a water immiscible amine with a total of at least 18 carbon atoms. Preferably the amine is a secondary, or tertiary amine, and most preferably in a tertiary amine. Said binding of lactic acid product assists in effecting said separation in said step (d). Said binding also helps in removing the lactic acid from the medium of said splitting, thereby facilitating said splitting (shifting the reaction forward). For that purpose said binding is preferably effected simultaneously with said splitting. The bound lactic acid product is stripped (e.g., by elution or back-extraction)

from its binding to said water immiscible base to form a lactic acid product. Preferably this stripping is effected by washing with water. Most preferably this washing is conducted at a temperature higher than that of the binding, preferably about 80° C. The binding of said lactic acid product to said water immiscible base in said preferred embodiment is selective. By adjustment of the ratio between the lactate content of said medium and the water immiscible base, according to methods known to persons versed in the art, non-acidic impurities in said fermentation liquor and most of the acidic impurities, that are less strong acids than lactic acid are left in the solution. The stripping of said lactic acid is also selective. In that case, most acids stronger than lactic acid and their anions, which were bound to the water immiscible base, remain bound to the water immiscible base and are not stripped with the lactic acid product. As a result, the lactic acid product is obtained in a relatively pure form, in most cases in a purity higher than 97%.

In a preferred embodiment, the salt splitting in step (c) is effected under $CO_2$ atmosphere, preferably at a pressure of at 690 kPa gauge (100 psig) and most preferably under a pressure of at least 1724 kPa gauge (250 psig). Preferably at least a part of said $CO_2$ ends up in the conjugated base, most preferably in the form of carbonate or bicarbonate.

In a most preferred embodiment, the splitting of the alkali metal lactate in step (c) is conducted according to Baniel's U.S. Pat. No. 5,510,526, the teachings of which are incorporated herein by reference.

Thus, in an highly preferred embodiment, calcium carbonate is used as a neutralizing agent in the fermentation and calcium lactate is formed in the fermentation liquor. Said fermentation liquor is reacted with sodium bicarbonate from a subsequent step at about equivalent ratio (two moles of sodium bicarbonate or a mole of sodium carbonate per mole of calcium lactate). Said reaction is effected by the addition of the bicarbonate into the fermentation medium and mixing for a few minutes at a temperature of about 70° C. The completion of the reaction is accelerated by the addition of sodium hydroxide, sweeping of nitrogen or air across the head space, sparging of nitrogen, air or steam through the medium or application of vacuum through the medium to create sub-atmospheric pressure. At the end of the reaction the precipitated calcium carbonate is separated by filtration, centrifugation, or decantation, treated by water-washing and re-used as a neutralizing agent in the fermentation. The sodium lactate solution formed is treated by active carbon and ion exchanger and concentrated to about 60%. The solution obtained is contacted with an extractant containing a tertiary amine with a total number of carbon atoms of at least 18 under $CO_2$ pressure of at least 1724 kPa gauge (250 psig). As a result, lactic acid is extracted into the extractant and sodium-carbonate precipitates. The lactic acid carrying extractant is back-extracted with water in a multi-stage counter-current mode at about boiling temperature or higher to obtain a solution of lactic acid, which after polishing purification with active carbon, is of high purity. The purity reaches the very high specifications of polymer grade. The sodium bicarbonate formed is re-used for conversion of calcium lactate in the fermentation liquor to sodium lactate and calcium carbonate.

In a preferred embodiment, said reaction of said alkali metal base with said medium in step (a) is conducted indirectly, preferably through ion exchange. According to one preferred embodiment said indirect reaction comprises the steps of (a) contacting a cation exchanger in an alkali metal form with said alkaline earth lactate containing medium whereby an alkali metal lactate is formed in said medium and said alkaline earth-metal ions are bound to said cation exchanger and (b) contacting said cation exchanger in alkaline earth-metal form with said alkali metal base to form an alkaline earth-metal base and to bind said alkali metal cations to said cation exchanger.

According to another preferred embodiment, said indirect reaction comprises the steps of (a) contacting an anion exchanger in a bicarbonate form with said alkaline earth lactate containing medium, whereby the bicarbonate of said alkaline earth-metal is formed in said medium and lactate ions are bound to said anion exchanger; and (b) contacting said anion exchanger in lactate form with bicarbonate anions to the anion exchanger.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

A liquor obtained by calcium carbonate neutralized fermentation, followed by biomass removal, is used. This liquor, containing calcium lactate in an amount equivalent to 166 g/L lactic acid, is heated to 70° C. Sodium bicarbonate from a previous stage is gradually added while mixing at a rate of 500 RPM. The amount of $NaHCO_3$ is slightly above stoichiometric (i.e. 2 moles per mole of calcium lactate contained in the liquor). Calcium carbonate precipitates and $CO_2$ evolves. The reaction yield, as determined by the concentration of calcium ions in the solution, is strongly dependent on the final pH. At pH of 7 it is 2–3000 ppm and drops significantly on approaching pH of about 8.5. Several methods were tested for pH adjustment to 8.5; removal of the evolving $CO_2$ by sweeping the head space or by sparging the solution with nitrogen or steam, using a small excess of $NaHCO_3$ and using a small amount of NaOH. In all those cases calcium ion concentrations are lower than 50 ppm and in few of them lower than 20 ppm. The latter represents a conversion yield of 99.95%.

Calcium carbonate filtration tests are conducted using #4 Whatmann filter. Filtration is quite easy, 100 ml. solutions filtered in an average of about 12 seconds.

The filtered calcium carbonate is washed with some water and re-used as a neutralizing agent in fermentation with no observed difficulties.

The sodium lactate containing filtrate is concentrated to 60% NaLa. Then it is mixed at 25° C., in a pressure vessel under $CO_2$ pressure of 30 atmospheres, with an extractant composed of 50% Alamine 336 (tricaprylyl amine produced by Henkel), 30% octanol and 20% kerosene. The volume ratio between the aqueous phase and the organic-phase is 1:1. After two hours mixing the organic phase is removed from the pressure vessel while still under $CO_2$ pressure. Then the pressure is released and the pressure vessel is opened. It contains an aqueous solution and a significant amount of NaHCO$_3$. The latter is separated by filtration and washed with a small amount of water. When re-used in a reaction with a calcium lactate containing liquor as described above, the same results are obtained and no separation of an organic phase is observed.

The organic phase is contacted with water at a temperature of 100° C. An aqueous solution of lactic acid is formed.

What is claimed is:

1. A process for producing lactic acid from a medium resulting from a fermentation of one carbohydrate, said medium containing an alkaline earth-metal salt of lactic acid, comprising:
    (a) converting said alkaline earth-metal salt of lactic acid into a water soluble alkali metal lactate salt by reacting said medium with a conjugated base of an alkali metal from a subsequent step to form said water soluble alkali metal lactate salt and a basic compound of said alkaline earth metal;
    (b) separating said water soluble alkali metal lactate salt and said basic compound of said alkaline earth metal;
    (c) splitting said water soluble alkali metal lactate to form a conjugated alkali metal base and a lactic acid product;
    (d) separating said conjugated alkali metal base and said lactic acid product;
    (e) re-using said separated conjugated alkali metal base to provide the conjugated base of an alkali metal in step (a); and,
    (f) reusing said basic compound of said alkaline earth metal, separated in step (b), to provide a neutralizing agent to form an alkaline earth-metal salt of lactic acid-containing medium for reaction according to step (a).

2. A process according to claim 1, wherein said alkaline earth-metal base separated in step (b), is re-used as a neutralizing agent in said fermentation.

3. A process according to claim 1, wherein said alkaline earth metal is selected from the group consisting of calcium and magnesium.

4. A process according to claim 1, wherein said alkaline earth metal is calcium.

5. A process according to claim 1, wherein said alkali metal is selected from the group consisting of sodium and potassium.

6. A process according to claim 1, wherein said alkali metal is sodium.

7. A process according to claim 1, wherein said alkali metal base or said alkaline earth-metal base comprises hydroxides, carbonates or bicarbonates of said metals.

8. A process according to claim 1, wherein said alkali metal base is a bicarbonate.

9. A process according to claim 1, wherein said alkaline earth metal base is a carbonate.

10. A process according to claim 1, wherein step (a) is conducted in the presence of a carbonate source comprising CO$_2$, bicarbonate anion, or carbonate anion.

11. A process according to claim 1, wherein step (a) is conducted at a temperature range of between 20° C. and the boiling point at a selected pressure.

12. A process according to claim 1, wherein the equivalent ratio between said alkaline earth-metal lactate in said medium and said alkali metal base is between 1:2 and 2:1.

13. A process according to claim 1, wherein said reaction in step (a) is conducted at pH of between 5 and 10.

14. A process according to claim 1, wherein said reaction in step (a) is conducted at pH of between 7 and 9.

15. A process according to claim 1, wherein the pH at the end of said reaction in step (a) is between 7 and 9.

16. A process according to claim 1, wherein said reaction in step (a) converts at least 80% of said alkaline earth-metal salt of lactic acid to a water soluble alkali metal lactate salt and to a basic compound of said alkaline earth metal.

17. A process according to claim 1, wherein said reaction in step (a) converts at least 99% of said alkaline earth-metal salt of lactic acid to a water soluble alkali metal lactate salt and to a basic compound of said alkaline earth metal.

18. A process according to claim 1, wherein said lactic acid product, formed in said step (c), is bound to a water immiscible base.

19. A process according to claim 18, wherein said water immiscible base is a tertiary amine with a total of at least 18 carbon atoms.

20. A process according to claim 18, wherein said bound lactic acid is stripped by contact with water at a temperature higher than that of binding to said water immiscible base.

21. A process according to claim 18, wherein said binding to said water immiscible base is conducted simultaneously with said splitting of said water soluble alkali metal lactate in step (c).

22. A process according to claim 1, wherein said splitting of said water soluble alkali metal lactate in step (c) is conducted under CO$_2$ pressure higher than 690 kPa gauge (100 psig).

23. A process according to claim 1, wherein said splitting of said water soluble alkali metal lactate in step (c) is conducted under CO$_2$ pressure higher than 1724 kPa gauge (250 psig).

24. A process according to claim 1, wherein the purity of said lactic acid product is at least 95%.

25. A process according to claim 1, wherein said reaction in step (a) is facilitated by an operation comprising subatmospheric pressure, sweeping of nitrogen or air across the head space, sparging of nitrogen, air or steam through the medium.

26. A process according to claim 1, wherein said basic compound of said alkaline earth-metal base or its derivative is separated in step (b) by crystallization.

27. A process according to claim 1, wherein said conjugated alkali metal base formed in said step (c) has water solubility of less than 20% at the temperature of said splitting step.

28. A process according to claim 1, wherein said conjugated alkali metal base is separated in step (d) by crystallization.

29. A process according to claim 1, wherein said alkali metal base from step (e), is purified prior to re-use in step (a).

30. A process according to claim 1, wherein said basic compound of said alkaline earth metal separated in step (b) is purified prior to use as a neutralizing agent.

31. A process according to claim 1, wherein at least a part of said alkaline earth-metal lactate in said medium is in solid form.

32. A process according to claim 1, wherein said alkaline earth-metal lactate in said medium is purified prior to step (a) by a step comprising washing, recrystallization from an aqueous solution, recrystallization from a solvent solution, treating said solution with active carbon, adsorbent or ion exchanger.

33. A process according to claim 1, wherein said reaction of said alkali metal base with said medium in step (a) is conducted indirectly.

34. A process according to claim 30, wherein said reaction is conducted through ion exchange.

35. A process according to claim 31, wherein said reaction comprises the steps of:
  (a) contacting a cation exchanger in an alkali metal form with said alkaline earth lactate containing medium, whereby an alkali metal lactate is formed in said medium and said alkaline earth-metal ions are bound to said cation exchanger, and
  (b) contacting said cation exchanger in alkaline earth-metal form with said alkali metal base to form an alkaline earth-metal base and to bind said alkali metal cations to said cation exchanger.

36. A process according to claim 31, wherein said reaction comprises the step of:
  (a) contacting an anion exchanger in a bicarbonate form with said alkaline earth lactate containing medium whereby the bicarbonate of said alkaline earth metal is formed in said medium and lactate ions are bound to said anion exchanger; and,
  (b) contacting said anion exchanger in lactate form with bicarbonate of said alkali metal to form a solution of a lactate of said alkali metal ion and to bind bicarbonate anions to the anion exchanger.

37. A process according to claim 1, wherein said basic compound of said alkaline earth metal is calcium carbonate and said calcium carbonate is converted to calcium oxide or hydroxide prior to said re-use.

38. A process according to claim 1, wherein the concentration of the cations of said alkaline earth metal in said alkali metal lactate salt is less than 1,000 ppm.

39. A process according to claim 1, wherein said reaction in said step (a) is facilitate by the addition of a second base of said alkali metal.

40. A process according to claim 1, wherein the water content in said reaction in step (a) is adjusted so that the concentration of the alkali metal lactate formed is at least 5%.

41. A process according to claim 1, wherein the water content in said reaction in step (a) is adjusted so that the concentration of the alkali metal lactate formed is at least 15%.

42. A process according to claim 2, wherein free lactic acid is separated from said fermentation medium prior to said step (a).

43. A process according to claim 1, wherein said lactic acid product is converted to polylactic acid.

44. A process according to claim 1, wherein step (a) is conducted in a continuous mode.

45. A process according to claim 1, wherein step (a) is conducted in a semi-continuous mode.

46. A process according to claim 1, wherein $CO_2$ formed in step (a) is re-used in the salt splitting of step (c).

47. A process according to claim 1, wherein a crystal habit modifier is used in step (a).

* * * * *